(12) United States Patent
Pierce et al.

(10) Patent No.: US 7,531,343 B2
(45) Date of Patent: May 12, 2009

(54) INDUCTION AND STABILIZATION OF ENZYMATIC ACTIVITY IN MICROORGANISMS

(75) Inventors: George E. Pierce, Canton, GA (US); Gene K. Drago, Atlanta, GA (US); Sangeeta Ganguly, Buffalo Grove, IL (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 11/669,011

(22) Filed: Jan. 30, 2007

(65) Prior Publication Data

US 2007/0184528 A1 Aug. 9, 2007

Related U.S. Application Data

(60) Provisional application No. 60/763,301, filed on Jan. 30, 2006, provisional application No. 60/822,570, filed on Aug. 16, 2006.

(51) Int. Cl.
*C12N 1/00* (2006.01)
*C12N 1/22* (2006.01)
*C12N 1/20* (2006.01)
*C12N 9/06* (2006.01)
*C12P 13/00* (2006.01)

(52) U.S. Cl. .................. 435/243; 435/128; 435/191; 435/252.1; 435/252.3

(58) Field of Classification Search ........................ None
See application file for complete search history.

(56) References Cited

U.S. PATENT DOCUMENTS

| 3,940,316 | A | 2/1976 | Commeyras et al. |
| 4,001,081 | A | 1/1977 | Commeyras et al. |
| 4,343,900 | A | 8/1982 | Watanabe |
| 4,880,739 | A | * 11/1989 | Yamada et al. ........... 435/129 |
| 5,807,730 | A | 9/1998 | Ito et al. |
| 5,863,750 | A | 1/1999 | Pierce |
| 6,060,265 | A | 5/2000 | Pierce |
| 6,132,985 | A | 10/2000 | Pierce |
| 6,133,421 | A | 10/2000 | Fallon et al. |
| 6,153,415 | A | 11/2000 | Oriel et al. |
| 6,214,603 | B1 | 4/2001 | Oriel et al. |
| 6,228,633 | B1 | 5/2001 | Oriel et al. |
| 6,242,242 | B1 | 6/2001 | Oriel et al. |
| 6,251,388 | B1 | 6/2001 | Durden |
| 6,287,828 | B1 | 9/2001 | Oriel et al. |
| 6,316,242 | B1 | 11/2001 | Endo et al. |
| 6,730,508 | B1 | 5/2004 | Ito et al. |
| 6,955,911 | B2 | 10/2005 | Ryuno et al. |
| 2003/0049807 | A1 | 3/2003 | Salvo et al. |
| 2004/0106165 | A1 | 6/2004 | Reisinger et al. |
| 2005/0014243 | A1 | 1/2005 | Uehara et al. |
| 2007/0184543 | A1 | 8/2007 | Pierce |

FOREIGN PATENT DOCUMENTS

| EP | 109083 | 5/1984 |
| EP | 0243 966 | 11/1987 |
| EP | 0243 967 | 11/1987 |
| EP | 0307926 | 3/1989 |
| JP | 54129190 | 10/1979 |
| JP | 2000470 | 1/1990 |
| JP | 5030983 | 2/1993 |
| JP | 5236977 | 9/1993 |
| JP | 8056684 | 3/1996 |
| JP | 8154691 | 6/1996 |
| JP | 8187092 | 7/1996 |

OTHER PUBLICATIONS

US Biological web page capture,http://www.usbio.net/Product.aspx?ProdSku=P3300, Nov. 2007, Composition of Peptone.*
Difco Manual of Dehydrated Culture Media and Reagents for Microbiological and Clinical Laboratory Procedures (1953) Ninth Edition. pp. 264 and 265 (double page scan attached).*
Hann et al., "5-Cyanovaleramide Production Using Immobilized Pseudomonas Chlororaphis B23", *Bioorg. Medicinal Chem.*, 1999, pp. 2239-2245, vol. 7.
Fawcett et al., "A Rapid and Precise Method for the Determination of Urea", *J. Clin. Path.*, 1960, pp. 156-159, vol. 13.
Kopf et al., "Key Role Of Alkanoic Acids On The Spectral Properties, Activity, and Active-Site Stability of Iron-Containing Nitrile Hydratase From Brevibacterium R312", *Eur. J. Biochem.*, 1996, pp. 239-244, vol. 240.
Nagasawa et al., "Optimum Culture Conditions for the Production of Benzonitrilase by Rhodococcus Rhodochrous" *Jl. Arch. Microbiol.*, 1988, pp. 89-94, vol. 150.
Nagasawa et al., "Occurrence of a Cobalt-Induced and Cobalt-Containing Nitrile Hydratase in Rhodococcus Rhodochrous", *Jl. Biochem. Biophys. Res. Comm.*, 1988, pp. 1008-1016, vol. 155.
Watanabe et al. "Screening, Isolation And Taxonomical Properties of Microorganisms Having Acrylonitrile Hydrating Activity", *Agric. Biol. Chem.*, 1987, pp. 3193-3199, vol. 51.
Badr et al., "Kinetics and Properties of L-Glutaminase and L-Asparaginase Activities of *Pseudomonas Ovalis,*" *Zbl. Bakt. II. Abt.*, 1976, pp. 489-496, vol. 131.
Bunch et al., "Biotransformation of Nitriles by Rhodococci," *Antonie van Leeuwenhoek*, 1998, pp. 89-97, vol. 74. Kluwer Academic Publishers, The Netherlands.
Foda et al., "Formation and Properties of L-Glutaminase and L-Asparaginase Activities in *Pichia Polymorpha,* " 1980, pp. 343-352, vol. 29, No. 4.

(Continued)

*Primary Examiner*—Lisa J Hobbs
(74) *Attorney, Agent, or Firm*—Fish & Richardson P.C.

(57) ABSTRACT

The present invention is directed to methods for inducing desired activity in enzymes or microorganisms capable of producing the enzymes. The invention is further directed to methods of stabilizing activity in microorganisms. In specific embodiments, the invention provides methods for inducing and stabilizing nitrile hydratase activity, amidase activity, and asparaginase I activity. The invention further provides compositions comprising enzymes or microorganisms having induced and/or stabilized activity.

33 Claims, 3 Drawing Sheets

OTHER PUBLICATIONS

Fisher et al., "*Bacillus Subtilis* 168 Contains Two Differentially Regulated Genes Encoding L-Asparaginase," 2002, pp. 2148-2154, vol. 184, No. 8.

Fournand et al. "Acyl Transfer Activity of an Amidase from *Rhodococcus* sp. Strain R312: Formation of a Wide Range of Hydroxamic Acids," *Applied and Environmental Microbiology*, 1998, pp. 2844-2852, vol. 64, No. 8.

Komeda, et al. "Characterization of the Gene Cluster of High-Molecular-Mass Nitrile Hyratase (H-NHase) Induced by its Reaction Produce in *Rhodococcus Rhodochrous* J1," *Proc. Natl. Acad. Sci.*, 1996, vol. 93, pp. 4267-4272.

Martinkova et al., "Nitrile- and Amide-Converting Microbial Enzymes: Stereo-, Regio-Chemoselectivity," *Biocatalysis and Biotransformation*, 2002, pp. 73-93, vol. 20, No. 2.

Nagasawa et al., "Optimum Culture Conditions for the Production of Coballt-Containing Nitrile Hydratase by *Rhodococcus Rhodochrous* J1," *Applied Microbiology and Biotechnology*, 1991, pp. 783-788, vol. 34.

Sonawane et al., "Utilization of Acidic Amino Acids and Their Amides by Pseudomanads: Role of Periplasmic Glutaminase-Asparaginase," *Arch Microbiol.*, 2003, pp. 151-159, vol. 179.

Sonawane et al., Identification of *Pseudomonas* Proteings Coordinately Induced by Acidic Amino Acids and Their Amides: A Two-Dimensional Electrophoresis Study, *Microbiology*, 2003, pp. 2909-2918, vol. 149.

Yamada et al. "Optimum Culture Conditions for Production by *Pseudomonas Chlororaphis* B23 of Nitrile Hydratase," *Agric.Biol. Chem.*, 1986, pp. 2859-2565, vol. 50, No. 11.

Sankhian et al., "Nitrile Hydratase of *Rhodococcus Rhodochrous* NHB-2: Optimisation of Conditions for Production of Enzyme and Conversion of Acrylonitrile to Acrylamide," *Asian Jr. of Microbiol. Biotech.*, 2003, pp. 217-223, vol. 5, No. 2.

Goda et al., "Discovery of a novel enzyme, isonitrile hydratase, involved in nitrogen-carbon triple bond cleavage" *J. Biol. Chem.* 276(26):23480-23485 (2001).

Kato, et al., "Nitrile hydratase involved in aldoxime metabolism from Rhodococcus sp. strain YH3-3 purification and characterization" *Eur. J. Biochem.* 263(3):662-70 (1999).

Nagasawa et al., "Nitrilase of *Rhodococcus rhodochrous* J1. Conversion into the active form by subunit association" *Eur. J. Biochem.* 267(1):138-44 (2000).

Soong, et al., "A novel amidase (half-amidase) for half-amide hydrolysis involved in the bacterial metabolism of cyclic imides" *Appl. Environ. Microbiol.* 66(5):1947-52 (2000).

Kobayashi and Shimizu, "Versatile nitrilases: Nitrile-hydrolysing enzymes" *FEMS Microbiology* 120:217-224 (1994).

Kobayashi and Shimizu, "Metalloenzyme nitrile hydratase: Structure, regulation and application to biotechnology" *Nature Biotechnology* 16:733-736 (1998).

Nagasawa, et al., "Superiority of *Pseudomonas chloroaphis* B23 nitrile hydratase as a catalyst for the enzymatic production of acrylamide" *Experientia* 45:1066-1070 (1989).

Nagasawa et al., "The superiority of the third-generation catalyst, *Rhodococcus rhodochrous* J1 nitrile hydratase, for industrial production of acrylamide" *Applied Microbiol. Biotechnol.* 40:189-195 (1993).

* cited by examiner

INDUCTION AND STABILIZATION OF ENZYMATIC ACTIVITY IN MICROORGANISMS

CROSS-REFERENCE TO RELATED APPLICATIONS

The present application claims priority to U.S. Provisional Patent Application No. 60/763,301, filed Jan. 30, 2006, and U.S. Provisional Patent Application No. 60/822,570, filed Aug. 16, 2006, both of which are incorporated herein by reference in their entirety.

FIELD OF THE INVENTION

The present invention is generally related to methods for growing microorganisms for enzyme production and compositions comprising enzymes or microorganisms having induced and/or stabilized activity. More particularly, the invention relates to methods for inducing a desired enzyme activity in microorganisms through use of specific growth media and to methods for stabilizing desired activity in an enzyme or a microorganism capable of producing the enzyme.

BACKGROUND OF THE INVENTION

Microorganisms, and their enzymes, have long been utilized as biocatalysts in the preparation of various products. The action of yeast in the fermentation of sugar to ethanol is an immediately recognizable example. In recent years, there has been a growing interest in the use of microorganisms and their enzymes in commercial activities not normally recognized as being amenable to enzyme use. One example is the use of microorganisms in industrial processes, particularly in the treatment of waste products.

Nitrile-containing compounds are used in a wide variety of commercial applications. For example, nitriles are used in the synthesis of many commercially useful compounds including amines, amides, amidines, carboxylic acids, esters, aldehydes, ketones, imines, and heterocyclics. Nitriles also are used as solvents, as herbicides, and in the synthesis of detergents and antiseptics. One of the more commercially important nitriles is acrylonitrile, which is used in the production of acrylamide, acrylic acid, acrylic fibers, copolymer resins, and nitrile rubbers.

The waste streams generated in the production of nitriles often contain high concentrations of hazardous nitrogen-containing compounds. For example, the waste streams can contain nitriles, such as acetonitrile, acrylonitrile, succinonitrile, and fumaronitrile. Further, such waste streams may also contain hazardous compounds, such as cyanides, acrylamides, acrolein, and cyanohydrins. As hazardous wastes generally cannot be released legally into the environment, methods for treating waste streams to remove or remediate one or more hazardous components are important in commercial production processes.

One method for treating nitrogen waste streams has been through the use of certain microorganisms that convert nitrile compounds into their corresponding amides or acids. For example, U.S. Pat. Nos. 3,940,316 and 4,001,081 disclose the use of nitrile hydratase microorganisms to produce acrylamide from acrylonitrile.

Generally, nitrile converting microorganisms degrade aliphatic nitriles in a two step reaction involving nitrile hydratase and amidase. In a first step, nitrile hydratase catalyzes the hydrolysis of the nitrile (or cyanohydrin) to the corresponding amide (or hydroxy acid). In a second step, amidase catalyzes the hydrolysis of the amide to the corresponding acid or hydroxy acid. Similarly, some microorganisms have been shown to degrade aromatic nitriles by directly converting these nitriles to their respective acid through the action of nitrilase.

Since the initial reports documenting the potential commercial utility of the biological conversion of acrylonitrile to acrylamide, the enzymes involved in the microbial degradation of nitriles have received considerable interest. The possibility of enzymatic preparation of chiral acids (such as hydroxy acids from cyanohydrin precursors) has also been a focus of much interest in this field. Despite promising results, the various potential applications of the nitrile hydratase/amidase conversion discussed above have not yet been fully exploited.

Another example of the growing use of microorganisms and their enzymes is in the formation of aspartic acid. Asparaginase I is an enzyme that catalyzes the hydrolysis of asparagine to aspartic acid, as shown below:

$HOOCCHNH_2CONH_2 + H_2O \rightarrow HOOCCHNH_2CH_2COOH + NH_3$

Asparaginase I can be found in bacteria, plants, and many animals; however, as human white blood cells do not possess the necessary asparagine synthase enzyme, the cells cannot make asparagine. It has thus been found that asparaginase I can be effective in the treatment of human malignant leukemia. Leukemia cells typically have low levels of asparagine synthase, the enzyme sometimes being completely absent. Leukemia cells, therefore, generally require an external source of asparagine. Since asparaginase I converts asparagine to aspartic acid, administering asparaginase I to a patient suffering from leukemia further limits the available source of asparagine for the cancerous cells and functions to weaken the cell making them more susceptible to chemotherapeutic treatments. Accordingly, asparaginase I is typically administered to a leukemia patient as part of a combination therapy with a chemotherapeutic agent.

Asparaginase I for use in such treatment is presently obtained from *E. coli* bacteria (in the form of a heterotetramer) and *Erwinia* bacteria (in the form of a homotetramer), but these sources each have disadvantages. For example, the asparaginase I obtained from *E. coli* is less effective than the asparaginase I obtained from *Erwinia*. However, it is much more difficult to produce asparaginase I using *Erwinia* than with *E. coli*. Further, these sources can result in the presence of Gram-negative toxins in the isolated enzyme, which is undesirable. Thus, there remains a need to increase asparaginase I production from a variety of microorganisms while avoiding simultaneous production of gram negative toxins, which can be harmful.

Stability, which is a key element for a practical biological catalyst, has been a significant hurdle to using nitrile hydratase and/or amidase in many commercial applications. While immobilization and chemical stabilizing agents are recognized approaches for improving enzyme stability, the current immobilization and stabilization techniques are still in need of further development. Accordingly, there remains a need in the art for method of inducing higher levels of enzymatic activity in a variety of microorganisms, particularly microorganisms capable of producing enzymes useful in the degradation of nitrile-containing compounds. Further, there is also a need for a method to improve the stabilization of key enzymes in the degradation of nitrile-containing compounds.

BRIEF SUMMARY OF THE INVENTION

The present invention is generally directed to methods for inducing and stabilizing enzymatic activity in microorganisms. The invention particularly makes use of nitrile hydratase producing microorganisms for inducing the production of a number of useful enzymes. For example, in certain embodiments, the invention provides methods useful for inducing production of nitrile hydratase (particularly at higher levels than previously possible), asparaginase I, and amidase from nitrile degrading microorganisms. In further embodiments, the invention provides methods of improving the stabilization of various enzymes, such as nitrile hydratase, asparaginase I, and amidase. The invention also provides bio-detoxifying catalysts (particularly incorporating enzymes, such as nitrile hydratase and amidase) that can maintain a commercially useful level of enzymatic activity over time. The biodetoxifying catalysts are particularly characterized in that the enzymatic activity of the biocatalysts can be induced and stabilized by their environment, as described herein.

The present invention is particularly characterized in that the methods disclosed herein can be used to induce enzymatic activity that is both of a level and stability that is useful in a practical biodetoxifying catalyst. The invention is further characterized by the ability to induce higher levels of asparaginase I from microorganisms, including (but not limited to) Gram-positive microorganisms, and to improve the stability of such asparaginase I activity.

The invention is particularly advantageous in that induction and stabilization of the microorganism can be accomplished without the requirement of introducing hazardous nitriles, such as acrylonitrile, into the environment. Previously, it was believed that induction of specific enzyme activity in certain microorganisms required the addition of chemical inducers. For example, in the induction of nitrile hydratase activity in *Rhodococcus rhodochrous* and *Pseudomonas chloroaphis*, it was generally necessary to supplement with hazardous chemicals, such as acetonitrile, acrylonitrile, acrylamide, and the like. Only according to the present invention, however, has it been surprisingly discovered that high enzymatic activity in nitrile hydratase producing microorganisms can by induced and stabilized with the use of non-hazardous media additives, such as amide containing amino acids, and derivatives thereof. More particularly, according to the invention, asparagine, glutamine, or combinations thereof, can be used as inducers with the complete exclusion of hazardous chemicals, such as acetonitrile, acrylonitrile, acrylamide, and the like. Thus, the present invention beneficially provides safer methods for production of commercially useful enzymes and microorganisms and their use in further methods, such as for detoxifying waste streams.

In preferred embodiments, the present invention provides for significant increases in the production and stability of a number of enzymes, and the microorganisms capable of producing the enzymes, using modified media, immobilization, and stabilization techniques, as described herein. For example induction and stabilization can be increased through use of media comprising amide-containing amino acids, or derivatives thereof.

In one aspect, the invention comprises a method for growing a nitrile hydratase producing microorganism. The method preferentially comprises culturing the microorganism in a medium comprising one or more amide containing amino acids or derivatives thereof. In specific embodiments, the nitrile hydratase producing microorganism comprises bacteria from the genus *Rhodococcus*. In preferred embodiments, the amide containing amino acids are selected from the group consisting of asparagine, glutamine, or combinations thereof.

In other embodiments, the invention provides a method for inducing a desired enzyme activity in a nitrile hydratase producing microorganism. Preferably, the method comprises culturing the nitrile hydratase producing microorganism in a medium comprising one or more amide containing amino acids or derivatives thereof. In specific embodiments, the enzyme activity induced by the method comprises nitrile hydratase activity, amidase activity, or asparaginase I activity. The methods of the invention can comprise further process steps, such as recovering the cultured microorganism having the desired enzyme activity, recovering an enzyme having the desired activity, affixing the microorganism, or cells therefrom, to a substrate, and cross-linking cells from the microorganism.

In still further embodiments, the invention particularly provides methods for stabilizing a desired activity in an enzyme or a microorganism capable of producing the enzyme. In one embodiment, such methods comprise contacting the enzyme, or a microorganism capable of producing the enzyme, with one or more amide containing amino acids.

In further embodiments of the invention, the enzyme, or the microorganism capable of producing the enzyme, can be immobilized. Such immobilization can function to affix the enzyme, microorganism, or cells to a substrate to facilitate ease of handling. In other embodiments, such immobilization can actually function to stabilize the induced activity, thus extending the time during which the induced activity can be utilized. The immobilization can comprise surface attachment of the enzyme, microorganism, or cells to a substrate. Alternately, the immobilization can comprise at least partially entrapping the enzyme, microorganism, or cells within a substrate or through cross-linking cells, such as with glutaraldehyde. This beneficially allows for presentation of an immobilized material with induced activity (e.g., a catalyst) in such a manner as to facilitate reaction of the catalyst with an intended material and recovery of a desired product while simultaneously retaining the catalyst in the reaction medium and in a reactive mode.

In particular embodiments, the substrate comprises a polymeric material, which is preferably selected from the group consisting of alginate and amide-containing polymers. Other substrate materials are also encompassed by the invention. Stabilized activity according to the invention is preferentially characterized by maintenance of a specific activity percentage in relation to the initial activity. For example, in one embodiment, the desired activity of the enzyme, or the microorganism capable of producing the enzyme, is stabilized such that the desired activity after a time of at least 30 days at a temperature of about 25° C. is maintained at a level of at least about 50% of the initial activity exhibited by the enzyme or the microorganism capable of producing the enzyme.

In still further embodiments, the invention provides methods for preparing an enzyme or microorganism having a specific enzymatic activity. For example, in one embodiment, the invention provides methods for preparing an enzyme or microorganism having nitrile hydratase activity. In particular, the method comprises inducing nitrile hydratase activity in a microorganism by culturing the microorganism in a medium comprising one or more amide containing amino acids or derivatives thereof, and recovering the enzyme or microorganism having nitrile hydratase activity. In further embodiments, the invention provides methods for preparing an enzyme or microorganism having asparaginase I activity or amidase activity.

The invention is still further characterized by the ability to multiply induce enzymatic activity in microorganisms such that the microorganisms, or the enzymes produced thereby, are capable of degrading a plurality of compounds. Thus, in one embodiment, the inventive method comprises multiply inducing nitrile hydratase activity toward a plurality of nitrile containing compounds in a microorganism by culturing the microorganism in a medium comprising one or more amide containing amino acids or derivatives thereof. Optionally, the method further comprises recovering the enzyme or microorganism having nitrile hydratase activity for degrading a plurality of nitrile containing compounds. Of course, in further embodiments, the invention provides methods of multiply inducing other types of activity.

In another aspect, the present invention provides a novel composition that is particularly useful in the methods of the invention, as well as for the production of various devices, such as biofilters. In one embodiment, the composition of the invention comprises: (a) a nutrient medium comprising one or more amide containing amino acids, or derivatives thereof, (b) one or more enzyme-producing microorganisms; and (c) one or more enzymes. Preferably, the enzymes are selected from the group consisting of nitrile hydratase, amidase, asparaginase I, and combinations thereof. In further embodiments, the one or more microorganisms comprise bacteria selected from the group consisting of genus *Rhodococcus*, genus *Brevibacterium*, and combinations thereof. In preferred embodiments, the one or more microorganisms can be at least partially immobilized on a substrate.

BRIEF DESCRIPTION OF THE DRAWINGS

The present invention is particularly described in reference to the following figures; however, such figures are provided to illustrate only preferred embodiments of the invention, and the invention is not intended to be limited thereto.

DETAILED DESCRIPTION OF THE INVENTION

Figure 1:
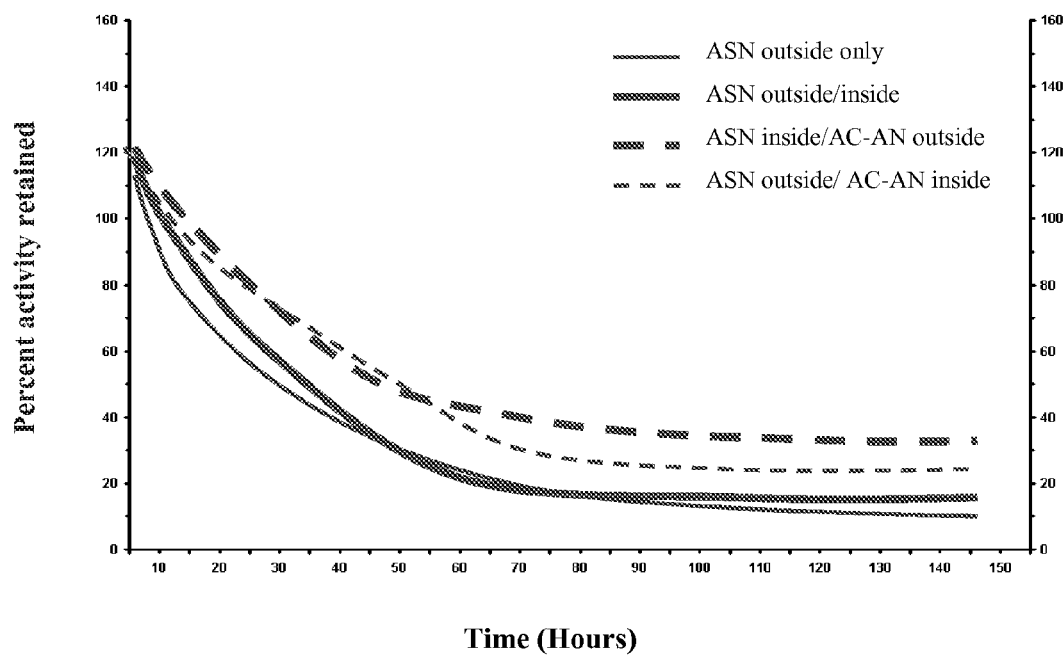
FIG. 1 is a graphical illustration of the stabilizing effect on nitrile hydratase activity provided by immobilization in calcium alginate in one embodiment according to one method of the invention.

The present inventions now will be described more fully hereinafter with reference to specific embodiments of the invention and particularly to the various drawings provided herewith. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention arises from the surprising finding that specific enzymatic activity can be induced and stabilized through addition of amide containing amino acids, or derivatives thereof, to a culture or composition comprising specific enzymes or microorganisms capable of producing such enzymes. Moreover, further stabilization can be achieved through immobilization methods, such as affixation, entrapment, and cross-linking. In specific embodiments, methods are provided for inducing higher levels of nitrile hydratase and amidase from nitrile degrading microorganisms (including nitrile hydratase producing microorganisms) and of improving the stability of nitrile hydratase.

The inventive methods described herein also provide for further methods useful in the detoxification of compositions containing nitrile compounds through conversion of the nitrile moieties into amides and/or acids. Such methods may be used to remove unwanted nitrile compounds from various compositions, such as waste streams produced from manufacturing and production facilities.

The present invention generally provides methods for culturing microorganisms, preferentially inducing specific enzymatic activity. Preferably, the methods comprise culturing the microorganisms in a medium comprising one or more amide containing amino acids, or derivatives thereof In preferred embodiments, the amide containing amino acids are selected from the group consisting of asparagine, glutamine, derivatives thereof, or combinations thereof. For example, the amide-containing amino acids may include natural forms of asparagines, anhydrous asparagine, asparagine monohydrate, natural forms of glutamine, anhydrous glutamine, and/or glutamine monohydrate, each in the form of the L-isomer or DL-isomer.

The concentration of the amide containing amino acids, or derivatives thereof, in the medium can vary depending upon the desired end result of the culture. For example, a culture may be carried out for the purpose of producing microorganisms having a specific enzymatic activity. In other embodiments, a culture may be carried out for the purpose of forming and collecting a specific enzyme from the cultured microorganisms. In yet further embodiments, a culture may be carried out for the purpose of forming and collecting a plurality of enzymes having the same or different activities and functions.

The amount of the amide containing amino acids, or derivatives thereof, added to the growth medium or mixture can generally be up to about 10,000 ppm (i.e., about 1% by weight) based on the overall weight of the medium or mixture. The present invention is particularly beneficial, however, in that enzyme activity can be induced through addition of even lesser amounts. For example, in certain embodiments, the concentration of the amide containing amino acids, or derivatives thereof, is in the range of about 50 ppm to about 5,000 ppm, about 100 ppm to about 3,000 ppm, about 200 ppm to about 2,000 ppm, about 250 ppm to about 1500 ppm, about 500 ppm to about 1250 ppm, or about 500 ppm to about 1000 ppm.

Preferably, the amide containing amino acids, or derivatives thereof, are added to a nutritionally complete media. A suitable nutritionally complete medium generally is a growth medium that can supply a microorganism with the necessary nutrients required for its growth, which minimally includes a carbon and/or nitrogen source. One specific example of a useful medium is the commercially available R2A agar medium, which typically consists of agar, yeast extract, proteose peptone, casein hydrolysate, glucose, soluble starch, sodium pyruvate, dipotassium hydrogenphosphate, and magnesium sulfate. Another example of a nutritionally complete liquid medium useful according to the present invention is Yeast Extract Malt Extract Agar (YEMEA), which consists of glucose, malt extract, and yeast extract (but specifically excludes agar). Of course, any nutritionally complete medium useful in the art could be used according to the present invention, the above media being described for exemplary purposes only.

In further embodiments, the methods of the invention can comprise the use of further additives to the nutritionally complete media. Typically, the other supplements or nutrients useful according to the invention are those useful for assisting in greater cell growth, greater cell mass, or accelerated growth. For example, in one embodiment, the nutritionally complete medium can comprise a carbohydrate source in addition to any carbohydrate source already present in the nutritionally complete medium.

As described above, most media typically contain some content of carbohydrate (e.g., glucose); however, according to the present invention, it can be useful to include an additional carbohydrate source. The type of excess carbohydrate provided can depend upon the desired outcome of the culture. For example, in specific embodiments, the addition of carbohydrates, such as maltose or maltodextrin, has been found provide for improved induction of asparaginase I.

In another embodiment, cobalt, or a salt thereof, can be added to the mixture or media. For example, the addition of cobalt (e.g., cobalt chloride) to the media can be particularly useful for increasing the mass of the enzyme produced by the cultured microorganisms. In certain embodiments, cobalt, or a salt thereof, can be added to the culture medium such that the cobalt concentration is an amount up to about 100 ppm. Preferably, cobalt is present in a concentration of about 5 ppm to about 100 ppm, about 10 ppm to about 75 ppm, about 10 ppm to about 50 ppm, or about 10 ppm to about 25 ppm.

In yet further embodiments, urea, or a salt thereof, can be added to the mixture or media. In certain embodiments, urea, or a salt thereof, can be added to the culture medium such that the urea concentration is in an amount up to about 10 g/L. Preferably, urea is present in a concentration of about 5 g/L to about 100 g/L, about 10 g/L to about 75 g/L, about 10 g/L to about 50 g/L, or about 10 g/L to about 25 g/L. In specific embodiments, urea is present in a concentration of about 7.5 g/L.

The medium may also include further components without departing from the present invention. For example, other suitable medium components may include commercial additives, such as cottonseed protein, maltose, maltodextrin, and other commercial carbohydrates.

The present invention is particularly characterized in that induction and stabilization of enzymes, and microorganisms capable of producing the enzymes, can be achieved without the need for hazardous nitriles. As previously pointed out, the induction of many types of enzyme activity, such as nitrile hydratase activity, has traditionally included supplementation with nitriles, such as acetonitrile, acrylonitrile, succinonitrile, and the like. Moreover, if multiple induction was desired (i.e., induction of activity in a single enzyme to degrade two or more types of nitriles), it was generally necessary to include two or more types of hazardous nitriles. The present invention, particularly arising from the use of amide containing amino acids, and derivatives thereof, as enzymatic inducers eliminates the need for hazardous chemicals to facilitate single or multiple enzymatic induction. Particularly, the present invention is beneficial in that multiple induction is possible through the use of amide containing amino acids, or derivatives thereof, in the culture medium or mixture. Again, this is especially surprising as multiple nitrile compounds were previously required in the culture medium to induce enzyme activity toward two or more nitrile compounds. However, the present invention achieves this particularly useful characteristic through the use of completely safe amide containing amino acids. Thus, the present invention is particularly useful for preparing an enzyme or microorganism having activity for degrading a plurality of nitrile containing compounds. Moreover, the methods of the invention provide the ability to detoxify a variety of nitriles or amides, such as nitriles having a single C≡N moiety, dinitriles (compounds having two C≡N moieties), or compounds having multiple nitrile moieties (e.g., acrolein cyanohydrin). Such enzymes, or microorganisms, are herein referred to as being multiply induced.

While the present invention eliminates the need for hazardous chemicals for enzyme activity induction, the use of such further inducers is not excluded. For example, in specific embodiments, one or more nitriles could be used to assist in specific activity development. For example, media supplemented with succinonitrile and cobalt can be useful for induction of asparaginase I activity. However, the use of nitriles is not necessary for induction of asparaginase I activity. Rather, while the use of nitriles and other hazardous chemicals is certainly not preferred according to the invention, in specific embodiments, such use is possible.

A variety of microorganisms can be cultivated for use according to the present invention. Generally, any microorganisms capable of producing enzymes having useful activity, as described herein, can be used in the invention. In particular embodiments, the microorganisms useful according to the invention comprise microorganisms capable of producing nitrile hydratase.

As used herein, nitrile hydratase producing microorganisms are intended to refer to microorganisms that, while generally being recognized as being capable of producing nitrile hydratase, are also capable of producing one or more further enzymes. As further described herein, most microorganisms are capable of producing a variety of enzymes, such production often being determined by the environment of the microorganism. Thus, while microorganisms for use according to the invention may be disclosed as nitrile hydratase producing microorganisms, such language only refers to the known ability of such microorganisms to produce nitrile hydratase and does not limit the microorganisms to only the production of nitrile hydratase. On the contrary, a nitrile hydratase producing microorganisms useful according to the invention is a microorganism capable of producing at least nitrile hydratase (i.e., is capable of producing nitrile hydratase or nitrile hydratase and one or more further enzymes).

A number of nitrile hydratase producing microorganisms are known in the art. For example, bacteria belonging to the genus *Nocardia* [see Japanese Patent Application No. 54-129190], *Rhodococcus* [see Japanese Patent Application No. 2-470], *Rhizobium* [see Japanese Patent Application No. 5-236977], *Klebsiella* [Japanese Patent Application No. 5-30982], *Aeromonas* [Japanese Patent Application No. 5-30983], *Agrobacterium* [Japanese Patent Application No. 8-154691], *Bacillus* [Japanese Patent Application No. 8-187092], *Pseudonocardia* [Japanese Patent Application No. 8-56684], and *Pseudomonas* are non-limiting examples of nitrile hydratase producing microorganisms that can be used according to the invention.

Further, specific examples of microorganisms useful according to the invention include, but are not limited to, *Nocardia* sp., *Rhodococcus* sp., *Rhodococcus rhodochrous*, *Klebsiella* sp., *Aeromonas* sp., *Citrobacter freundii*, *Agrobacterium rhizogenes*, *Agrobacterium tumefaciens*, *Xanthobacter flavas*, *Erwinia nigrifluens*, *Enterobacter* sp., *Streptomyces* sp., *Rhizobium* sp., *Rhizobium loti*, *Rhizobium legminosarum*, *Rhizobium merioti*, *Candida guilliermondii*, *Pantoea agglomerans*, *Klebsiella pneumoniae subsp. pneumoniae*, *Agrobacterium radiobacter*, *Bacillus smithii*, *Pseudonocardia thermophila*, *Pseudomonas chloroaphis*, *Pseudomonas erythropolis*, *Brevibacterium ketoglutamicum*, *Rhodococcus erythropolis*, and *Pseudonocardia thermophila*. In particularly preferred embodiments, microorganisms used according to the invention comprise *Rhodococcus* sp. DAP 96253 and DAP 96255 and *Rhodococcus rhodochrous* DAP 96622.

In further embodiments, microorganisms useful according to the invention can also include transformants. In particular, the transformants can be any host wherein a nitrile hydratase gene cloned from a microorganism known to include such a gene, is inserted and expressed. For example, U.S. Pat. No. 5,807,730 describes the use of *Escherichia coli* as a host for the MT-10822 bacteria strain (FERM BP-5785). Of course, other types of genetically engineered bacteria could be used according to the invention so long as the bacteria are capable of producing one or more enzymes useful in the invention, as described herein.

Not all species within a given genus exhibit the same type of enzyme activity and/or production. Thus, it is possible to have a genus generally know to include strains capable of exhibiting a desired activity but have one or more species that do not generally exhibit the desired activity. Thus, in still further embodiments, host microorganisms can include strains of bacteria that are not specifically known to have the desired activity but are from a genus known to have specific strains capable of producing the desired activity. Such strains can have transferred thereto one or more gene useful to cause the desired activity. Non-limiting examples of such strains include *Rhodococcus equi* and *Rhododoccus globerulus* PWD1.

Enzymatic activity, as used herein, generally refers to the ability of an enzyme to act as a catalyst in a process, such as the conversion of one compound to another compound. Likewise, the desired activity referred to herein can include the activity of one or more enzymes being actively expressed by one or more microorganisms.

In certain embodiments, activity can be referred to in terms of "units" per mass of enzyme or cells (typically based on the dry weight of the cells, e.g., units/mg cdw). A "unit" generally refers to the ability to convert a specific content of a compound to a different compound under a defined set of conditions as a function of time. In specific embodiments, 1 "unit" of nitrile hydratase activity can relate to the ability to convert 1 µmol of acrylonitrile to its corresponding amide per minute, per milligram of cells (dry weight) at a of pH 7.0 and a temperature of 30° C. Similarly, 1 unit of amidase activity can relate to the ability to convert 1 µmol of acrylamide to its corresponding acid per minute, per milligram of cells (dry weight) at a pH of 7.0 and a temperature of 30° C. Further, 1 unit of asparaginase I activity can relate to the ability to convert 1 µmol of asparagine to its corresponding acid per minute, per milligram of cells (dry weight) at a pH of 7.0 and a temperature of 30° C.

In preferred embodiments, the present invention is particularly characterized by the ability to induce a desired activity that is greater than possible using previously known methods.

For example, in one embodiment, the invention allows for inducing nitrile hydratase activity in a nitrile hydratase producing microorganism that is greater than or equal to the activity produced in the same microorganism by induction with a nitrile containing compound. In preferred embodiments, the nitrile hydratase activity produced is greater than the activity produced in the same microorganism by induction with a nitrile containing compound. For example, the nitrile hydratase activity produced according to the methods of the invention can be at least 5% greater than the activity produced in the same microorganism by induction with a nitrile containing compound. Preferably, the nitrile hydratase activity produced according to the methods of the invention is at least 10%, at least 12%, or at least 15% greater than the activity produced in the same microorganism by induction with a nitrile containing compound.

The microorganisms useful according to the invention can be selected from known sources (such as those described above) or can comprise newly isolated microorganisms. In one embodiment of the invention, microorganisms suitable with the present invention may be isolated and identified as useful microorganism strains by growing strains in the presence of a mixture of amide containing amino acids, or derivatives thereof. The microorganism can be isolated or selected or obtained from known sources or can be screened from future sources based on the ability to detoxify a mixture of nitriles or a mixture of nitrile and amide compounds or a mixture of amides to the corresponding amide and/or acid after multiple induction according to the present invention. In light of the disclosure provided herein, it would be a matter of routine experimentation for one of skill in the art to carry out an assay to determine whether the microorganism was useful according to the present invention. For example, in one assay, the presence of nitrile hydratase or amidase activity can be determined through detection of free ammonia. See Fawcett, J. K. and Scott, J. E., 1960, "A Rapid and Precise Method for the Determination of Urea", *J. Clin. Pathol.* 13:156-159, which is incorporated herein by reference.

The present invention beneficially provides methods for cultivating microorganisms, particularly nitrile hydratase producing microorganisms. In certain embodiments, the invention is directed to methods for inducing a desired enzyme activity in microorganisms, such as nitrile hydratase producing enzymes. Preferentially, the method comprises culturing a nitrile hydratase producing microorganism in a medium comprising one or more amide containing amino acids, or derivatives thereof. In one embodiment, the invention provides a method for inducing nitrile-detoxification activity using a medium supplemented with amide containing amino acids, or derivatives thereof, which preferably include asparagine, glutamine or a combination thereof. More particularly, the method comprises culturing the microorganism in the medium and optionally collecting the cultured microorganisms or enzymes produce by the microorganisms.

The microorganisms can be cultured and harvested according to methods useful for achieving optimal biomass. In certain embodiments, such as when cultured on agar plates, the microorganisms can be cultured for a period of at least about 24 but generally less than six days. When cultured in a fermentor, the microorganisms are preferably cultured in a minimal medium for a period of about 1 hour to about 48 hours, about 1 hour to about 20 hours, or about 16 hours to about 23 hours. If a larger biomass is desired, the microorganisms can be cultured in the fermentor for longer time periods. At the end of the culture period, the cultured microorganisms are typically collected and concentrated, for example, by scraping, centrifuging, filtering, or any other method known to those skilled in the art.

In specific embodiments, the microorganisms can be cultured under further specified conditions. For example, culturing is preferably carried out at a pH between about 3.0 and about 11.0, more preferably between about 6.0 and about 8.0. The temperature at which culturing is performed is preferably between about 4° C. and about 55° C., more preferably between about 15° C. and about 37° C. Further, the dissolved oxygen tension is preferentially between about 0.1% and 100%, preferably between about 4% and about 80%, and more preferably between about 4% and about 30%. The dissolved oxygen tension may be monitored and maintained in the desired range by supplying oxygen in the form of ambient air, pure oxygen, peroxide, and/or other compositions which liberate oxygen.

It is also possible according to the present invention to separate the steps of microorganism growth and enzyme activity induction. For example, it is possible according to the invention to grow one or more microorganisms on a first medium that does not include supplementation necessary to induce enzyme activity. Such can be referred to as a growth phase for the microorganisms. In a second phase (i.e., an induction phase), the cultured microorganisms can be transferred to a second medium comprising supplementation necessary to induce enzyme activity. Such second medium would preferentially comprise the amide containing amino acids, or derivatives thereof, as described herein.

Similarly, the induction supplements can be added at any time during cultivation of the desired microorganisms. For example, the media can be supplemented with amide containing amino acids, or derivatives thereof, prior to beginning cultivation of the microorganisms. Alternately, the microorganisms could be cultivated on a medium for a predetermined amount of time to grow the microorganism, and amide containing amino acids, or derivatives thereof, could be added at one or more predetermined times to induce the desired activity in the microorganisms. Moreover, the amide containing amino acids, or derivatives thereof, could be added to the growth medium (or to a separate mixture including the previously grown microorganisms) to induce the desired activity in the microorganisms after the growth of the microorganisms is complete.

As noted above, the methods of the invention are particularly useful for inducing a desired enzyme activity. Many types of microorganisms, including those described herein, are capable of producing a variety of enzymes having a variety of activities. As is generally understood in the art, the type of enzyme activity induced in microorganism cultivation can vary depending upon the strain of microorganism used, the method of growth used, and the supplementation used with the growth media. The present invention surprisingly allows for induction of a variety of enzyme activities through the use of amide containing amino acids, or derivatives thereof. In preferred embodiments, the present invention provides for induction of one or more enzymes selected from the group consisting of nitrile hydratase, amidase, and asparaginase I. In specific embodiments, such enzymes are induced by culturing one or more bacteria from the genus *Rhodococcus* in a medium comprising one or more amide containing amino acids, or derivatives thereof.

In particular embodiments, the invention allows for the simultaneous induction of both nitrile hydratase and amidase. This is particularly useful for industrial applications, such as the treatment of nitrile-containing waste streams. Such treatment requires a first treatment to convert nitriles to amides and a second treatment to convert amides to acids. The ability to simultaneously produce nitrile hydratase and amidase would remove the need to separately prepare the enzymes and would essentially allow for a single treatment step.

In further embodiments, the invention particularly provides for the induction of asparaginase I activity. Surprisingly, it has been discovered that asparaginase I activity can be induced in *Rhodococcus rhodochrous*, DAP 96622 (Gram positive), or *Rhodococcus* sp., DAP 96253 (Gram positive), in medium supplemented with amide containing amino acids, or derivatives thereof. Other strains of *Rhodococcus* can also preferentially be used according to this embodiment of the invention. Yet other strains capable of producing asparaginase I include *Pseudomonas chloroaphis* (ATCC 43051) (Gram positive), *Pseudomonas chloroaphis* (ATCC 13985) (Gram positive), *Rhodococcus erythropolis* (ATCC 47072) (Gram positive), and *Brevibacterium ketoglutamicum* (ATCC 21533) (Gram positive), Thus, the present invention is further beneficial in that it allows for the induction of asparaginase I activity in Gram-positive bacteria.

The desired activity (e.g., nitrile hydratase, amidase, or asparaginase I activity) of the harvested microorganisms, once induced according to the methods described herein, can beneficially be stabilized. Commercial use of enzymes for the treatment of waste water, as well as other commercial uses of various enzymes, is generally limited by the instability of the induced activity. For examples, fresh cells will typically lose at least 50% of their initial activity within 24 hours at a temperature of 25° C. Thus, when cells are to be used as a catalyst, the cells must be made at the time of need and cannot be stored for future use. Nitrile hydratase activity can be stabilized through addition of nitrile containing compounds; however, this again necessitates the use of undesirable, hazardous chemicals. The present invention again solves this problem. For example, cells having induced nitrile hydratase activity can be stabilized according to the present invention, without the need for hazardous chemicals, such that the cells have a viable enzyme activity for a time period of up to one year. Thus, the present invention stabilizes enzymes, or microorganisms capable of producing such enzymes, such that the practical activity of the induced activity is extended well beyond the typical period of useful activity.

In one embodiment, such stabilization is provided by addition of one or more amide containing amino acids, or derivatives thereof. The amide containing amino acids, or derivatives thereof, can be added to the microorganisms at the time of culturing the microorganisms or can be added to a mixture comprising enzyme activity induced microorganisms, cells, or subunit enzymes. Any amide containing amino acids, or derivatives thereof, as previously described herein can be used for stabilization of induced activity according to this embodiment of the invention.

In further embodiments, stabilization can be provided, according to the invention, by immobilizing the cultured microorganism, or cells therefrom. For example, cells harvested from the microorganisms, enzymes harvested from the microorganisms, or the induced microorganisms themselves, can be immobilized to a substrate as a means to stabilize the induced activity. In certain embodiments, the enzymes, cells, or microorganisms are at least partially entrapped in the substrate.

Any substrate generally useful for affixation of cells, enzymes, or microorganisms can be used according to the invention. In one embodiment, the substrate comprises alginate, or salts thereof. Alginate is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks. In a preferred embodiment, calcium alginate is used as the substrate. Particularly preferred is calcium alginate that has been cross-linked, such as with polyethyleneimine, to form a hardened calcium alginate substrate. Further description of such immobilization techniques can be found in Bucke, C. (1987), "Cell Immobilization in Calcium Alginate", *Methods in Enzymology*, volume 135, Part B (ed. K. Mosbach) pp. 175-189, which is incorporated herein by reference. The stabilization effect of immobilization using polyethyleneimine cross-linked calcium alginate is illustrated in FIG. 1, which is further described below in Example 2.

Figure 2:
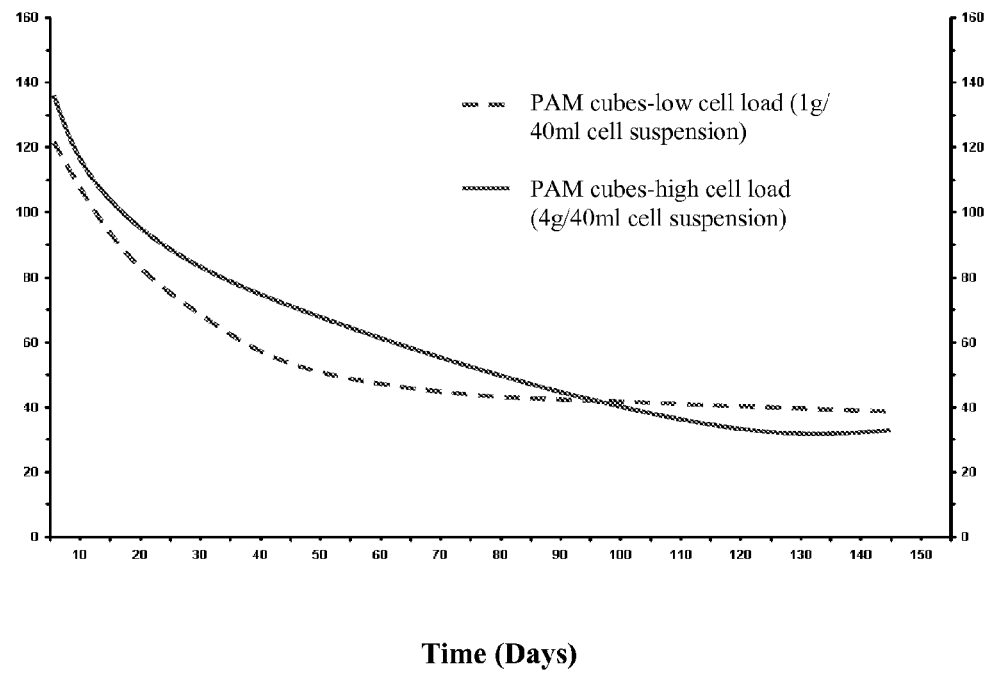
FIG. 2 is a graphical illustration of the stabilizing effect on nitrile hydratase activity provided by immobilization in polyacrylamide in one embodiment according to one method of the invention.

In another embodiment, the substrate comprises an amide-containing polymer. Any polymer comprising one or more amide groups could be used according to the invention. In one preferred embodiment, the substrate comprises a polyacrylamide polymer. The stabilization effect of immobilization using polyacrylamide is illustrated in FIG. 2, which is further described below in Example 3.

Figure 4:
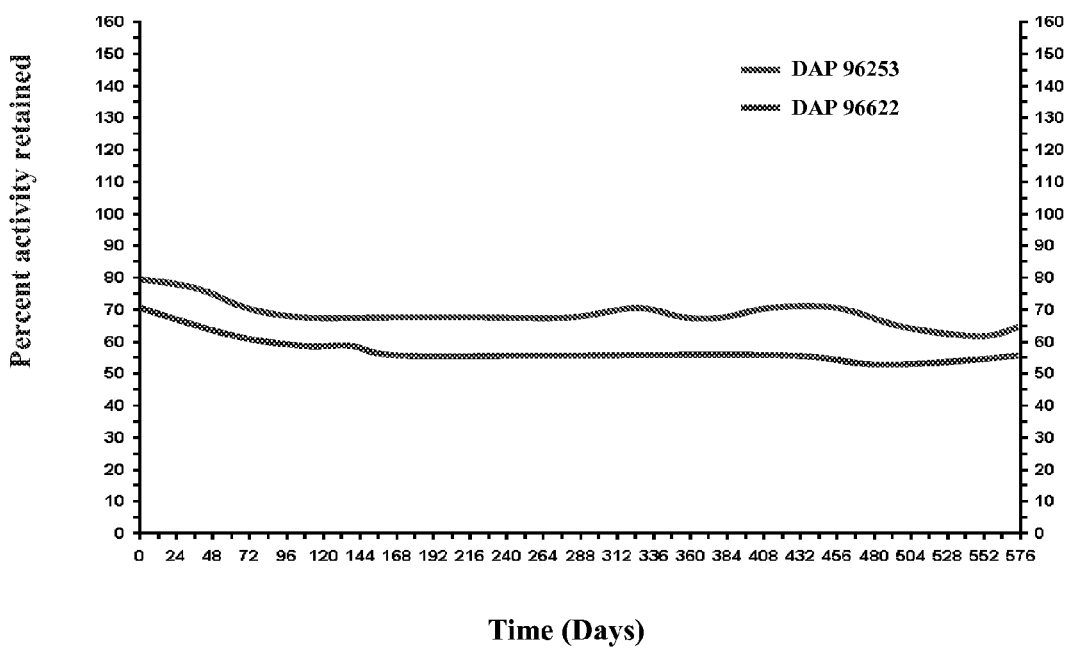
FIG. 4 is a graphical illustration of the stabilizing effect on nitrile hydratase activity provided by immobilization through glutaraldehyde cross-linking according to one method of the invention.

Stabilization can further be achieved, according to the invention, through cross-linking. For example, cells harvested from an induced microorganism can be chemically cross-linked to form agglutinations of cells. In one preferred embodiment, cells harvested from an induce microorganism are cross-linked using glutaraldehyde. For example, cells can be suspended in a mixture of de-ionized water and glutaraldehyde followed by addition of polyethyleneimine until maximum flocculation is achieved. The cross-linked cells (typically in the form of particles formed of a number of cells) can be harvested by simple filtration. Further description of such techniques is provided in Lopez-Gallego, et al., "Enzyme Stabilization by Glutaraldehyde Crosslinking of Absorbed Proteins on Aminated Supports", *J. Biotechnol.* 119:70-75, which is incorporated herein by reference. The stabilization effect of glutaraldehyde cross-linking is illustrated in FIG. 4, which is further described below in Example 5.

In another embodiment, the microorganisms can be encapsulated or immobilized rather than allowed to remain in the classic Brownian motion. Such immobilization facilitates collection, retention, and reuse of the microorganisms and generally comprises affixation of the microorganisms to a substrate. Such affixation can also facilitate stabilization of the microorganisms, as described above, or may be solely to facilitate ease of handling of the induced microorganisms or enzymes.

The microorganisms can be immobilized by any method generally recognized as useful for immobilization of microorganisms, such as sorption, electrostatic bonding, covalent bonding, and the like. Generally, the microorganisms are immobilized on a solid support which aids in the recovery of the microorganisms from a mixture or solution, such as a detoxification reaction mixture. Suitable solid supports include, but are not limited to granular activated carbon, compost, wood residue products, (e.g., wood chips, wood, nuggets, shredded pallets or trees), metal or metal oxide particles (e.g., alumina, ruthenium, iron oxide), ion exchange resins, DEAE cellulose, DEAE-SEPHADEX® polymer, ceramic beads, cross-linked polyacrylamide beads, cubes, prills, or other gel forms, alginate beads, κ-carrageenan cubes, as well as solid particles that can be recovered from the aqueous solutions due to inherent magnetic ability. The shape of the catalyst is variable (in that the desired dynamic properties of the particular entity are integrated with volume/surface area relationships that influence catalyst activity). In preferred embodiments, the induced microorganism is immobilized in alginate beads that have been cross-linked with polyethyleneimine or is immobilized in a polyacrylamide-type polymer.

In specific embodiments, the invention provides methods for detoxifying a mixture of nitrites by converting the nitrites to the corresponding amides or acids. In one embodiment, the method comprises applying a culture of nitrile degrading microorganisms to a mixture of nitrites and multiply inducing the microorganisms with a mixture of amide containing amino acids, or derivatives thereof, for a sufficient amount of time to convert the nitrites to the corresponding amides. Alternatively, the method comprises applying multiply induced microorganisms to a mixture of nitrites for a sufficient amount of time to convert the nitrites to the corresponding amides.

When the microorganisms are applied to a waste stream, the microorganisms may be growing (actively dividing) or resting (not actively dividing). When the method entails application of an actively growing culture of microorganisms, the application conditions are preferably such that bacterial growth is supported or sustained. When the method entails application of a culture of microorganisms which are not actively dividing, the application conditions are preferably such that enzymatic activities are supported.

In specific embodiments, the present invention can be used to treat waste streams from a production plant having waste that typically contains high concentrations of nitrites, cyanohydrin(s), or other chemicals subject to enzymatic degradation. For example, the invention provides a detoxification method to detoxify a mixture of nitrile compounds or a mixture of nitrile and amide compounds in an aqueous waste stream from a nitrile production plant. Further, the present invention could be used for treatment of waste streams in the production of acrylonitrile butadiene styrene (ABS), wherein acrylonitrile is used in the production of the ABS.

The present invention also provides a biofilter that can be used in the detoxification of mixtures of nitrile compounds, mixtures of nitrile and amide compounds and mixtures of amide compounds in effluents such as air, vapors, aerosols, and water or aqueous solutions. For example, if volatile nitrile compounds are present, the volatiles may be stripped from solid or aqueous solution in which they are found and steps should be carried out in such a way that the volatiles are trapped in a biofilter. Once trapped, the volatiles can be detoxified with a pure culture or an extract of a microorganism, as described herein.

The present invention also provides for kits comprising a culture of a microorganism which has been multiply induced and is able to detoxify a mixture of nitrile compounds, a mixture of nitrile and amide compounds, or a mixture of amide compounds. The microorganism can be actively dividing or lyophilized and can be added directly to an aqueous solution containing the nitrile and/or amide compounds. In a preferred embodiment, the kit comprises an induced lyophilized sample. The microorganism also can be immobilized onto a solid support, as described herein. Other kit components can include, for example, a mixture of induction supplements, as described herein, for induction of the microorganisms, as well as other kit components, such as vials, packaging components, and the like, which are known to those skilled in the art.

EXPERIMENTAL

The present invention will now be described with specific reference to various examples. The following examples are not intended to be limiting of the invention and are rather provided as exemplary embodiments.

Example 1

Nitrile Hydratase and Amidase Induction

The induction of nitrile hydratase activity and amidase activity in *Rhodococcus* sp., strain DAP 96253, was evaluated using multiple types of inducers (1000 ppm). Three different samples were cultured in YEMEA medium containing 10 ppm cobalt and 7.5 g/L urea and supplemented with acrylonitrile, asparagine, or glutamine. The specific nitrile hydratase activity and the specific amidase activity in each sample was evaluated, and the results are provided below in Table 1, with activities provided in units/mg cdw (cell dry weight). One unit of nitrile hydratase activity relates to the ability to convert 1 μmol of acrylonitrile to its corresponding amide per minute, per milligram of cells (dry weight) at a of pH 7.0 and a temperature of 30° C. One unit of amidase activity relates to the ability to convert 1 μmol of acrylamide to its corresponding acid per minute, per milligram of cells (dry weight) pH of 7.0 and a temperature of 30° C.

TABLE 1

| Supplement | Nitrile Hydratase Activity (Units/mg cdw) | Amidase Activity (Units/mg cdw) |
|---|---|---|
| Acrylonitrile | 162.23 | 7.59 |
| Asparagine | 170.50 | 13.24 |
| Glutamine | 173.45 | 10.39 |

As seen in Table 1, the use of asparagine or glutamine as an inducer for nitrile hydratase activity exceeds the ability of acrylonitrile to induce such activity. Moreover, the use of glutamine as an inducer resulted in amidase activity approximately 37% greater than the amidase activity resulting from the use of acrylonitrile, and asparagine provided approximately 74% greater activity than acrylornitrile.

Example 2

Stabilization of Nitrile Hydratase Activity Using Calcium Alginate Immobilization Testing was performed to evaluate the relative stability of cells induced for nitrile hydratase activity using asparagine in the culture medium. *Rhodococcus* sp., strain DAP 96253, was cultured using a standard culture medium alone or supplemented with asparagine. Cells were recovered from the culture and immobilized in calcium alginate beads (2-3 mm diameter). To prepared the beads, 25 g of a 4% sodium alginate solution (1 g sodium alginate in 24 ml of 5 mM TRIS-HCl-pH 7.2) was prepared, and 25 mg of sodium meta-periodate was dissolved therein (stirred at 25° C. for 1 hr or until all alginate has dissolved). The cells for immobilization were suspended in 50 mM TRIS-HCl to a final volume of 50 ml, and the cell solution was added to the alginate mixture while stirring. Beads were formed by extruding the mixture through a 27G hypodermic needle into 500 ml of 0.1M $CaCl_2$. The beads were cured for 1 hr in the $CaCl_2$ solution and washed with water.

Four samples were prepared for evaluation: Sample 1—beads formed with cells cultured without asparagine but with asparagine added to the mixture including the beads; Sample 2—beads formed with cells cultured with asparagine and having asparagine added to the mixture including the beads; Sample 3—beads formed with cells cultured with asparagine and having a mixture of acrylonitrile and acetonitrile added to the mixture including the beads; and Sample 4—beads formed with cells cultured with acrylonitrile and acetonitrile and having asparagine added to the mixture including the beads. In samples 3 and 4, acrylonitrile and acetonitrile were added in a concentration of 500 ppm each. In each of samples 1-4, asparagine was added at 1000 ppm.

The immobilized cells were maintained for a time of about 150 hours and periodically evaluated for the remaining nitrile hydratase activity. The results of the test are illustrated in FIG. 1. For evaluation of stabilized activity, equivalent amounts of cells were tested, and the activity of an equivalent aliquot of whole cells at time 0 was set as 100%. Equivalent aliquots of catalyst were incubated at the appropriate temperature. At the appropriate times, an entire aliquot was removed from incubation and the enzyme activity determined. For the first 10 hours samples were evaluated every 2 hours. From 10-60 hours samples were evaluated every 4 hours and thereafter, samples were evaluated every 12 hours.

As seen in FIG. 1, immobilization of induced cells in calcium alginate provides stabilization of nitrile hydratase activity that is very similar to the level of stabilization achievable using hazardous nitrile containing compounds but without the disadvantages (e.g., health and regulatory issues).

Example 3

Stabilization of Nitrile Hydratase Activity Using Polyacrylamide Immobilization

Testing was performed to evaluate the relative stability of cells induced for nitrile hydratase activity using asparagine in the culture medium. *Rhodococcus* sp., strain DAP 96253, was cultured using a standard culture medium supplemented with asparagine. Cells were recovered from the culture and immobilized in cross-linked polyacrylamide cubes (2.5 mm×2.5 mm×1 mm). The polyacrylamide solution was prepared, and the desired loading of cells was added. The polyacrylamide with the cells was cross-linked to form a gel, which was cut into the noted cubes. No further known stabilizers were added to the polyacrylamide. Two samples were prepared for evaluation: Sample 1—cubes with low cell load (prepared with suspension comprising 1 g of cells per 40 mL of cell suspension); and Sample 2—cubes with high cell load (prepared with suspension comprising 4 g of cells per 40 mL of cell suspension).

The immobilized cells were maintained for a time of about 150 days and periodically evaluated for the remaining nitrile hydratase activity. The results of the test are illustrated in FIG. 2. For evaluation of stabilized activity, equivalent amounts of cells were tested, and the activity of an equivalent aliquot of whole cells at time 0 was set as 100%. Equivalent aliquots of catalyst were incubated at the appropriate temperature. At the appropriate times, an entire aliquot was removed from incubation and the enzyme activity determined. For the first 10 hours samples were evaluated every 2 hours. From 10-60 hours samples were evaluated every 4 hours. From 5 days to 40 days samples were evaluated every 12 hours. From 40 to 576 days, samples were evaluated on average every 10 days.

As seen in FIG. 2, cells stabilized using polyacrylamide maintained activity as much as 150 hours after induction. Moreover, polyacrylamide-immobilized cells loaded at a low concentration still exhibited 50% of the initial activity at about 45 hours after induction, and polyacrylamide-immobilized cells loaded at a high concentration still exhibited 50% of the initial activity at about 80 hours after induction.

Example 4

Stabilization of Nitrile Hydratase Activity Using Calcium Alginate or Polyacrylamide Immobilization Testing was performed to evaluate the relative stability of cells induced for nitrile hydratase activity using asparagine in the culture medium. The testing specifically compared the stabilization provided by immobilization in polyacrylamide or calcium alginate. *Rhodococcus* sp., strain DAP 96622, was cultured using a standard culture medium supplemented with asparagine to induce nitrile hydratase activity. Cells were recovered from the culture for immobilization.

Test Sample 1 was prepared by immobilizing the asparagine induced cells in polyacrylamide cubes (2.5 mm×2.5 mm×1 mm) using the method described in Example 3. As a comparative, cells separately induced using acrylonitrile were also immobilized in polyacrylamide cubes for evaluation.

Test Sample 2 was prepared by immobilizing the asparagine induced cells in calcium alginate beads (2-3 mm diameter) using the method described in Example 2. As a comparative, one sample was prepared using actual nitrile containing waste water as the inducing supplement (denoted NSB/WWCB). A second comparative was prepared using, as the inducer, a synthetic mixture containing the dominant nitriles and amides present in an acrylonitrile production waste stream (also including ammonium sulfate and expressly excluding hydrogen cyanide) (denoted FC w/AMS w/o HCN).

Figure 3:
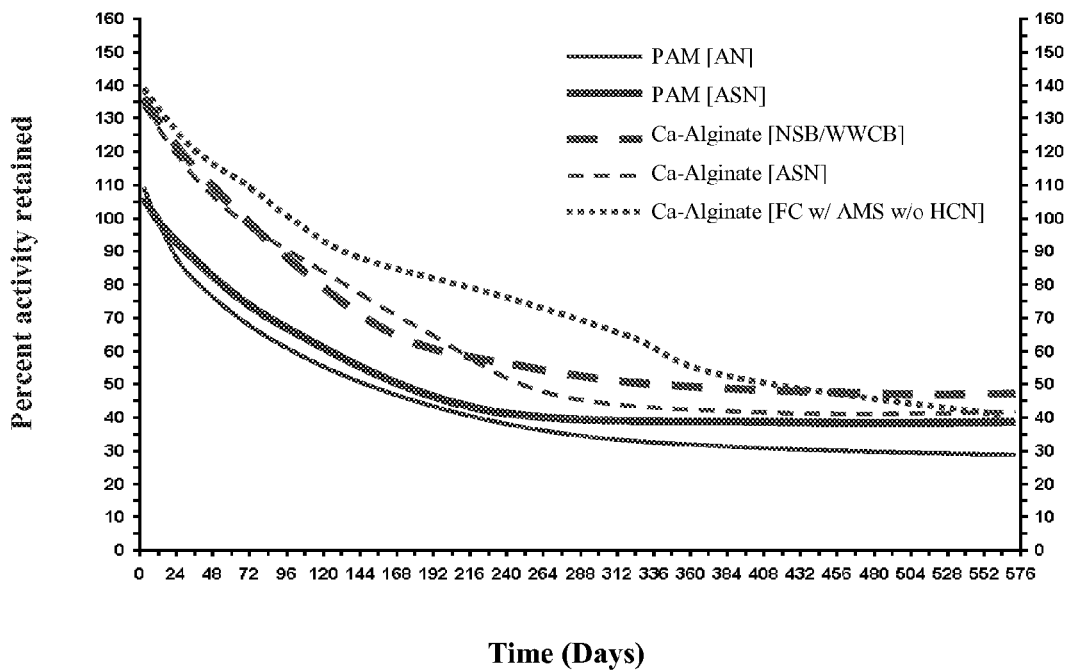
FIG. 3 is a graphical illustration of the stabilizing effect on nitrile hydratase activity provided by immobilization in hardened, polyethyleneimine cross-linked calcium alginate or polyacrylamide in further embodiments according to one method of the invention.

The immobilized cells were maintained for a time of about 576 days and periodically evaluated for the remaining nitrile hydratase activity. The results of the test are illustrated in FIG. 3. For evaluation of stabilized activity, equivalent amounts of cells were tested. The activity of an equivalent aliquot of whole cells at time 0 was set as 100%. Equivalent aliquots of catalyst were incubated at the appropriate temperature. At the appropriate times, an entire aliquot was removed from incubation and the enzyme activity determined. For the first 10 hours samples were evaluated every 2 hours. From 10-60 hours samples were evaluated every 4 hours. From 5 days to 40 days samples were evaluated every 12 hours. From 40 to 576 days, samples were evaluated on average every 10 days.

Example 5

Stabilization of Nitrile Hydratase Activity Using Glutaraldehyde Immobilization

Testing was performed to evaluate the relative stability of cells induced for nitrile hydratase activity using asparagine in the culture medium. The testing specifically compared the stabilization provided by immobilization via glutaraldehyde cross-linking. *Rhodococcus* sp., strain DAP 96253, and *Rhodococcus rhodochrous*, strain DAP 96622, were separately cultured using a standard culture medium supplemented with asparagine to induce nitrile hydratase activity. Cells were recovered from the culture and cross-linked using glutaraldehyde, as described herein.

The immobilized cells were maintained for a time of about 576 days and periodically evaluated for the remaining nitrile hydratase activity. The results of the test are illustrated in FIG. 4. For evaluation of stabilized activity, equivalent amounts of cells were tested. The activity of an equivalent aliquot of whole cells at time 0 was set as 100%. Equivalent aliquots of catalyst were incubated at the appropriate temperature. At the appropriate times, an entire aliquot was removed from incubation and the enzyme activity determined. For the first 10 hours samples were evaluated every 2 hours. From 10-60 hours samples were evaluated every 4 hours. From 5 days to 40 days samples were evaluated every 12 hours. From 40 to 576 days, samples were evaluated on average every 10 days.

As seen in FIG. 4, both strains immobilized via glutaraldehyde cross-linking exhibited somewhat less initial activity in comparison to other stabilizations methods described above. However, both strains immobilized via glutaraldehyde cross-linking exhibited excellent long-term stabilization maintaining as much as 65% activity after 576 days.

Example 6

Effect of Asparagine and Glutamine on Growth of Nitrile Hydratase Producing Microorganisms The relative growth of various nitrile hydratase producing microorganisms was evaluated. All strains were grown on YEMEA medium containing 7.5 g/L of urea and 10 ppm cobalt (provided as cobalt chloride) supplemented with asparagine (ASN), glutamine (GLN), or both asparagine and glutamine. The asparagine and glutamine were added 3.8 mM. Growth temperature was in the range of 26° C. to 30° C. Growth was evaluated by visual inspection and graded on the following scale: (−) meaning no detectable growth; (+/−) meaning scant growth; (+) meaning little growth; (++) meaning good growth; (+++) meaning very good growth; and (++++) meaning excellent growth. The results are provided below in Table 2.

TABLE 2

| Strain | ATCC # | Growth Temp. (° C.) | Growth Medium Supplementation | | |
|---|---|---|---|---|---|
| | | | ASN | GLN | ASN + GLN |
| *Pseudomonas chloroaphis* | 43051 | 30 | + | − | + |
| *Pseudomonas chloroaphis* | 13985 | 26 | + | + | ++ |
| *Brevibacterium ketoglutaricum* | 21533 | 30 | + | + | + |
| *Rhodococcus erythropolis* | 47072 | 26 | ++ | ++ | +++ |
| *Rhodococcus* sp. DAP 96253 | 55899 | 30 | ++++ | ++++ | ++++ |

TABLE 2-continued

| Strain | ATCC # | Growth Temp. (° C.) | Growth Medium Supplementation | | |
|---|---|---|---|---|---|
| | | | ASN | GLN | ASN + GLN |
| Rhodococcus rhodochrous DAP 96622 | 55898 | 26 | ++++ | ++++ | ++++ |

Example 7

Effect of Asparagine and Glutamine on Nitrile Hydratase and Amidase Production The induction of nitrile hydratase production and amidase production in various nitrile hydratase producing microorganisms was evaluated. All strains were grown on YEMEA medium containing 7.5 g/L of urea and 10 ppm cobalt (provided as cobalt chloride) supplemented with asparagine (ASN), glutamine (GLN), or both asparagine and glutamine. The asparagine and glutamine were added 3.8 mM. As a comparative, enzyme production with no supplementation was also tested. Growth temperature was in the range of 26° C. to 30° C. The nitrile hydratase level in Units per mg of cell dry weight was evaluated, and the results are provided in Table 3. The amidase level in Units per mg of cell dry weight was evaluated, and the results are provided in Table 4.

TABLE 3

| Strain | ATCC # | Growth Temp. (° C.) | Nitrile Hydratase Level (Units/mg cdw) Based on Growth Medium Supplementation | | | |
|---|---|---|---|---|---|---|
| | | | ASN | GLN | ASN + GLN | None |
| Pseudomonas chloroaphis | 43051 | 30 | 28 | No growth | 45 | 49 |
| Pseudomonas chloroaphis | 13985 | 26 | 14 | 0 | 8 | 30 |
| Brevibacterium ketoglutaricum | 21533 | 30 | 30 | 37 | 42 | 34 |
| Rhodococcus erythropolis | 47072 | 26 | 48 | 42 | 55 | 55 |
| Rhodococcus sp. DAP 96253 | 55899 | 30 | 155 | 135 | 152 | 82 |

TABLE 3-continued

| Strain | ATCC # | Growth Temp. (° C.) | Nitrile Hydratase Level (Units/mg cdw) Based on Growth Medium Supplementation | | | |
|---|---|---|---|---|---|---|
| | | | ASN | GLN | ASN + GLN | None |
| Rhodococcus rhodochrous DAP 96622 | 55898 | 26 | 158 | 160 | 170 | 63 |

TABLE 4

| Strain | ATCC # | Growth Temp. (° C.) | Amidase Level (Units/mg cdw) Based on Growth Medium Supplementation | | | |
|---|---|---|---|---|---|---|
| | | | ASN | GLN | ASN + GLN | None |
| Pseudomonas chloroaphis | 43051 | 30 | 0 | No growth | 0 | 0 |
| Pseudomonas chloroaphis | 13985 | 26 | 14 | 0 | 8 | 4 |
| Brevibacterium ketoglutaricum | 21533 | 30 | 0 | 0 | 3 | 2 |
| Rhodococcus erythropolis | 47072 | 26 | 9 | 14 | 6 | 2 |
| Rhodococcus sp. DAP 96253 | 55899 | 30 | 13 | 7 | 10 | 4 |
| Rhodococcus rhodochrous DAP 96622 | 55898 | 26 | 10 | 6 | 12 | 5 |

Example 8

Effect of Asparagine and Glutamine on Asparaginase I Production

The induction of asparaginase I production in various nitrile hydratase producing microorganisms was evaluated. All strains were grown on YEMEA medium containing 7.5 g/L of urea and 10 ppm cobalt (provided as cobalt chloride) supplemented with asparagine (ASN), glutamine (GLN), or both asparagine and glutamine. The asparagine and glutamine were added 3.8 mM. As a comparative, enzyme production was also evaluated with supplementation was with acrylonitrile (AN), acrylamide (AMD) or acrylonitrile and acrylamide. Growth temperature was in the range of 26° C. to 30° C. The asparaginase I level in Units per mg of cell dry weight was evaluated, and the results are provided in Table 5.

TABLE 5

| Strain | ATCC # | Growth Temp. (° C.) | Asparaginase I Level (Units/mg cdw) Based on Growth Medium Supplementation | | | | | |
|---|---|---|---|---|---|---|---|---|
| | | | AN | AMD | AN/AMD | ASN | GLN | ASN/GLN |
| Pseudomonas chloroaphis | 43051 | 30 | — | — | — | 18.4 | No Growth | 18.7 |
| Pseudomonas chloroaphis | 13985 | 26 | 2 | 0 | 3 | 0 | 0 | 1 |
| Brevibacterium ketoglutaricum | 21533 | 30 | 14.6 | 15.4 | 13.6 | 19.1 | 20.3 | 17.8 |
| Rhodococcus erythropolis | 47072 | 26 | — | 0 | 0 | 1 | 2 | 0 |

TABLE 5-continued

| Strain | ATCC # | Growth Temp. (°C.) | Asparaginase I Level (Units/mg cdw) Based on Growth Medium Supplementation | | | | | |
|---|---|---|---|---|---|---|---|---|
| | | | AN | AMD | AN/AMD | ASN | GLN | ASN/GLN |
| Rhodococcus sp. DAP 96253 | 55899 | 30 | 7.8 | 2 | 7.4 | 12.5 | 11.1 | 13.9 |
| Rhodococcus rhodochrous DAP 96622 | 55898 | 26 | 8.2 | 7.8 | 10.1 | 12.3 | 10 | 13.8 |

Example 9

Induction of Asparaginase I Activity in *Rhodococcus* sp. DAP 96253 Cells

Figure 5:
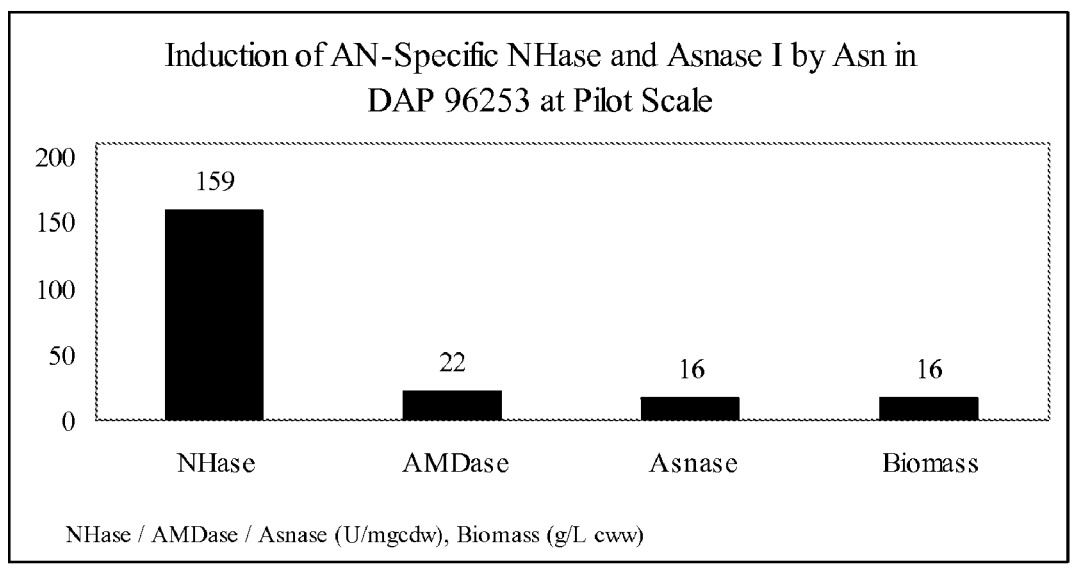
FIG. 5 is a graphical illustration of the asparaginase I activity in *Rhodococcus* sp. DAP 96253 cells induced with asparagine according to one embodiment of the invention.

*Rhodococcus* sp. DAP 96253 were grown using biphasic medium as the source of inoculum for a 20 liter fermentation. The supplemental addition of medium/carbohydrate (either YEMEA, dextrose or maltose) was made to the modified R2A medium, containing cottonseed hydrolysate substituted for the Proteos Peptone 3 (PP3). Asparagine (0.15M solution) was added at a continuous rate of 1000 μl/min beginning at t=10 h. At the end of the fermentation run, 159 units per milligram cell dry weight of acrylonitrile specific nitrile hydratase, 22 units of amidase per milligram cell dry weight, and 16 g/l cell packed wet weight were produced. The amount of various enzymes produced is provided in FIG. 5. As can be seen therein, 159 units of nitrile hydratase, 22 units of acrylamidase, and 16 units of asparaginase I per milligram cell dry weight was produced by the DAP 96253 cells.

Example 10

Effect of Media Composition on Asparaginase I Production in *Rhodococcus* sp. DAP 96253 Cells Testing was performed to evaluate the effect on asparaginase I activity based upon the inducer used. In particular, testing was performed using asparagine, glutamine, succinonitrile, and isovaleronitrile as inducers (all added at 1000 ppm each). As can be seen in Table 6, asparagine was able to induce asparaginase I activity of 24.6 units/mg cell dry weight. Glutamine or succinonitrile also showed an ability to induce asparaginase I activity. Higher asparaginase I activity was obtained when maltose was added to YEMEA. The inclusion of Cobalt (5-50 ppm) in the medium also resulted in improvements when combined with either glucose or maltose.

TABLE 6

Asparaginase I levels in *Rhodococcus* sp. DAP 96253 Grown in Medium with Carbohydrate Supplement

| | YEMEA - Glucose | | YEMEA - Maltose | |
|---|---|---|---|---|
| Inducer | Without Cobalt | With Cobalt | Without Cobalt | With Cobalt |
| Asparagine | 5.3 | 6.5 | 8.7 | 24.6 |
| Glutamine | 1.5 | 1.9 | 9.3 | 8.1 |

TABLE 6-continued

Asparaginase I levels in *Rhodococcus* sp. DAP 96253 Grown in Medium with Carbohydrate Supplement

| | YEMEA - Glucose | | YEMEA - Maltose | |
|---|---|---|---|---|
| Inducer | Without Cobalt | With Cobalt | Without Cobalt | With Cobalt |
| Succinonitrile | 6.5 | 8.5 | 11.0 | 10.0 |
| Isovaleronitrile | 3.5 | 2.9 | 6.8 | 7.0 |

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for inducing an enzyme activity selected from the group consisting of nitrile hydratase activity, amidase activity, asparaginase I activity, and combinations thereof in a nitrile hydratase producing microorganism comprising culturing the nitrile hydratase producing microorganism in a medium comprising at least 50 ppm of one or more amide containing amino acids selected from the group consisting of asparagine, glutamine, asparagine derivatives, glutamine derivatives, and combinations thereof, wherein the nitrile hydratase producing microorganism comprises bacteria selected from the group consisting of genus *Rhodococcus*, genus *Brevibacterium*, genus *Pseudonocardia*, genus *Nocardia* and combinations thereof.

2. The method of claim 1, wherein the enzyme activity includes nitrile hydratase activity.

3. The method of claim 1, wherein the nitrile hydratase producing microorganism comprises bacteria from the genus *Rhodococcus*.

4. The method of claim 1, wherein the nitrile hydratase producing microorganism comprises bacteria selected from the group consisting of *Rhodococcus rhodochrous* DAP 96622, *Rhodococcus* sp. DAP 96253, and combinations thereof.

5. The method of claim 1, wherein the one or more amide containing amino acids include asparagine.

6. The method of claim 1, wherein the one or more amide containing amino acids are present in a concentration of 50 ppm to 5000 ppm.

7. The method of claim 1, wherein the medium is free of any nitrile containing compounds.

8. The method of claim 1, further comprising immobilizing the microorganism.

9. The method of claim 1, wherein the induced nitrile hydratase producing microorganism has an enzyme activity greater than or equal to the activity of the same enzyme when induced in a medium comprising a nitrile containing compound.

10. The method of claim 1, wherein the induced nitrile hydratase producing microorganism has an enzyme activity that is at least 5% greater than the activity of the same enzyme when induced in a medium comprising a nitric containing compound.

11. The method of claim 1, wherein the medium further comprises cobalt.

12. The method of claim 1, wherein the medium further comprises urea.

13. The method of claim 1, wherein the medium further comprises maltose or maltodextrin.

14. The method of claim 1, wherein the amide containing amino acids include asparagine and asparagine derivatives, and wherein the asparagine and asparagine derivatives include natural forms of asparagine, anhydrous asparagine, asparagine monohydrate, and L-isomers and D-isomers thereof.

15. The method of claim 1, wherein the amide containing amino acids include glutamine and glutamine derivatives, and wherein the glutamine and glutamine derivatives include natural forms of glutamine, anhydrous glutamine, glutamine monohydrate and L-isomers and D-isomers thereof.

16. A method for inducing an enzyme activity selected from the group consisting of nitrile hydratase activity, amidase activity, asparaginase I activity, and combinations thereof in a nitrile hydratase producing microorganism comprising culturing the nitrile hydratase producing microorganism in a medium comprising urea and at least 50 ppm of one or more amide containing amino acids selected from the group consisting of asparagine, glutamine, asparagine derivatives, glutamine derivatives, and combinations thereof, wherein the nitrile hydratase producing microorganism comprises bacteria from the genus *Pseudomonas*.

17. The method of claim 16, wherein the medium further comprises cobalt.

18. The method of claim 16, wherein the medium is free of any nitrile containing compounds.

19. The method of claim 16, wherein the medium further comprises maltose or maltodextrin.

20. The method of claim 16, wherein the one or more amide containing amino acids are present in a concentration of 200 ppm to 2000 ppm.

21. The method of claim 16, wherein the one or more microorganisms are at least partially immobilized.

22. A method for inducing an enzyme activity selected from the group consisting of nitrile hydratase activity, amidase activity, asparaginase I activity, and combinations thereof in a nitrile hydratase producing microorganism comprising culturing the nitrile hydratase producing microorganism in a medium comprising at least 50 ppm of one or more amide containing amino acids selected from the group consisting of asparagine, glutamine, asparagine derivatives, glutamine derivatives, and combinations thereof, wherein the nitrile hydratase producing microorganism comprises bacteria from the genus *Pseudomonas*, and wherein the microorganism is at least partially immobilized.

23. The method of claim 22, wherein the medium further comprises cobalt.

24. The method of claim 22, wherein the medium is free of any nitrile containing compounds.

25. The method of claim 22, wherein the medium further comprises maltose or maltodextrin.

26. The method of claim 22, wherein the one or more amide containing amino acids are present in a concentration of 200 ppm to 2000 ppm.

27. A method for inducing an enzyme activity selected from the group consisting of nitrile hydratase activity, amidase activity, asparaginase I activity, and combinations thereof in a nitrile hydratase producing microorganism comprising culturing the nitrile hydratase producing microorganism in a medium comprising at least 50 ppm of one or more amide containing amino acids selected from the group consisting of asparagine, glutamine, asparagine derivatives, glutamine derivatives, and combinations thereof, wherein the medium is free of any nitrile containing compounds.

28. The method of claim 27, wherein the medium further comprises cobalt.

29. The method of claim 27, wherein the medium further comprises maltose or maltodextrin.

30. The method of claim 27, wherein the one or more amide containing amino acids are present in a concentration of 200 ppm to 2000 ppm.

31. The method of claim 27, wherein the one or more microorganisms are at least partially immobilized.

32. The method of claim 27, wherein the nitrile hydratase producing microorganism comprises bacteria selected from the group consisting of genus *Rhodococcus*, genus *Brevibacterium*, genus *Pseudomonas*, genus *Pseudonocardia*, genus *Nocardia*, and combinations thereof.

33. The method of claim 27, wherein the nitrile hydratase producing microorganism comprises bacteria selected from the group consisting of *Rhodococcus rhodochrous* DAP 96622, *Rhodococcus* sp. DAP 96253, and combinations thereof.

* * * * *